(12) United States Patent
Roe

(10) Patent No.: US 9,116,083 B2
(45) Date of Patent: Aug. 25, 2015

(54) TEST TAP

(71) Applicant: Daniel Leigh Roe, Hawkestone (CA)

(72) Inventor: Daniel Leigh Roe, Hawkestone (CA)

( * ) Notice: Subject to any disclaimer, the term of this patent is extended or adjusted under 35 U.S.C. 154(b) by 234 days.

(21) Appl. No.: 13/694,242

(22) Filed: Nov. 13, 2012

(65) Prior Publication Data

US 2014/0130616 A1   May 15, 2014

(51) Int. Cl.
*G01N 1/20* (2006.01)

(52) U.S. Cl.
CPC ............... *G01N 1/2035* (2013.01); *G01N 1/20* (2013.01); *G01N 2001/205* (2013.01)

(58) Field of Classification Search
CPC .. G01N 1/20; G01N 1/2035; G01N 2001/205
USPC ............... 73/863.57, 863.71–863.72, 863.86, 73/864.63, 864.73
See application file for complete search history.

(56) References Cited

U.S. PATENT DOCUMENTS

| | | | | |
|---|---|---|---|---|
| 2,692,502 A * | 10/1954 | Warren | ...................... | 73/863.71 |
| 3,390,580 A * | 7/1968 | Taylor | .................... | 73/864.63 X |
| 3,798,972 A * | 3/1974 | Collins, Jr. | ................. | 73/863.71 |
| 3,812,722 A * | 5/1974 | Soudelier | ............ | G01N 1/2035 |
| 4,873,876 A * | 10/1989 | Sheridan et al. | ........... | 73/863.86 |
| 5,341,692 A * | 8/1994 | Sher et al. | ................... | 73/864.63 |
| 6,035,727 A * | 3/2000 | Preston | ................... | 73/863.86 X |
| 8,033,187 B2 * | 10/2011 | Sann et al. | ....... | G01N 2001/205 |
| 8,978,492 B1 * | 3/2015 | Haworth et al. | ........... | 73/864.63 |
| 2009/0013805 A1 * | 1/2009 | Zollinger | ................... | 73/863.86 |
| 2012/0111128 A1 * | 5/2012 | Wisser | ................ | G01N 1/2035 |
| 2013/0025725 A1 * | 1/2013 | Gotch | ............. | G01N 2001/205 |
| 2015/0007648 A1 * | 1/2015 | Theron et al. | ........ | G01N 1/2035 |

FOREIGN PATENT DOCUMENTS

| | | | | | |
|---|---|---|---|---|---|
| CN | 102661878 A | * | 9/2012 | ............... | G01N 1/20 |
| CN | 202522447 U | * | 11/2012 | ............... | G01N 1/20 |
| JP | 57194334 A | * | 11/1982 | ................ | 73/864.73 |
| JP | 2004256171 A | * | 9/2004 | ............... | B67D 1/14 |
| RU | 2269107 C2 | * | 1/2006 | ............... | G01N 1/00 |
| WO | WO 2010121765 A1 | * | 10/2010 | ............... | G01N 1/20 |
| WO | WO 2011096823 A1 | * | 8/2011 | ........... | G01N 1/2035 |

* cited by examiner

*Primary Examiner* — Thomas P Noland

(57) ABSTRACT

A sampling system for use in a sampling station that includes a sampling device that is releasable connectable to a branch line so that it may be removed when not needed at that site via a releasable coupling. The device has a main tube connected to the releasable coupling via a valve that is manually operated through an operating tube that is connected to the main tube so that it also functions to clear the main tube.

4 Claims, 3 Drawing Sheets

US 9,116,083 B2

TEST TAP

FIELD OF INVENTION

The present invention relates to an improved test tap system for obtaining water samples from water systems such as municipal water systems for testing

BACKGROUND OF THE PRESENT INVENTION

The practice of tapping into a water distribution system to obtain a sample is common practice and is used by most if not all water systems particularly those distributing water for human consumption. In most of these systems the sampling site will have a branch inlet water line that extends from the main line and is used to deliver water to the test sample taking station. Flow to the station is generally controlled via a valve in the branch line to turn flow to the test station off or on. Most stations include a housing that has its bottom end below the surface of the ground to about the level of the branch line so that the branch line may enter and connect to the sample line adjacent to the bottom of the housing. The top of the housing is above ground and the sample line extends to a position adjacent to the top of the housing and that is easily accessed by an operator to take a sample. In one such system a flexible sample pipe that may be left in coiled position in the housing between uses is used as a sample line. In some cases a second valve is interposed between the branch line.

The present invention provides an improvement over these known devices in that it provides a sampling system that permit easy sample taking and draining of the system after sample taking is completed as well as easy coupling and decoupling of the sampling system to the branch line so that the sampling device of the present invention may removed from the housing and if desired used at another sampling site.

BRIEF DESCRIPTION OF THE PRESENT INVENTION

It is an object of the present invention to provide an improved water sampling station adapted to obtain a water sample with the sample obtaining device in operative position while permitting the sample obtaining device to be removed when in inoperative position.

Broadly the present invention relates to a water sampling system comprising a sample obtaining device for use in a water sampling station, said device comprising a main tube, a first portion of a releasable coupling connected to one end of said main tube via a sampling valve, an operating leaver for said valve, a operating tube connected adjacent to one end of said operating tube to said operating lever so that movement of said operating tube moves said sampling valve between an open and a closed position, a main tube emptying line connecting said one end of said operating tube to said main tube at a location immediately adjacent to said sampling valve and opposite ends of said main and operating tubes are spaced from their respective one ends and to permit easy access thereto when said device is in operative position.

Preferably said sampling system includes a water sampling station that includes a fixed casing wherein said sample obtaining device in operative position is received and each of said opposite ends are accessible through an opening into said casing and a branch inlet line for water to be sampled passes into said casing and mounts a second portion of said releasable coupling to which said first portion is releasable coupled when said device is in operative position.

Preferably said sample obtaining device further includes a drain line that extends from adjacent to said opposite ends to a remote end that is on the side of said first portion of said releasable coupling remote from said main tube.

BRIEF DESCRIPTION OF THE SEVERAL VIEWS OF THE DRAWINGS

Further features, objects and advantages will be evident from the following detailed description of the preferred embodiments of the present invention taken in conjunction with the accompanying drawings in which.

DETAILED DESCRIPTION OF THE INVENTION

Figure 2:
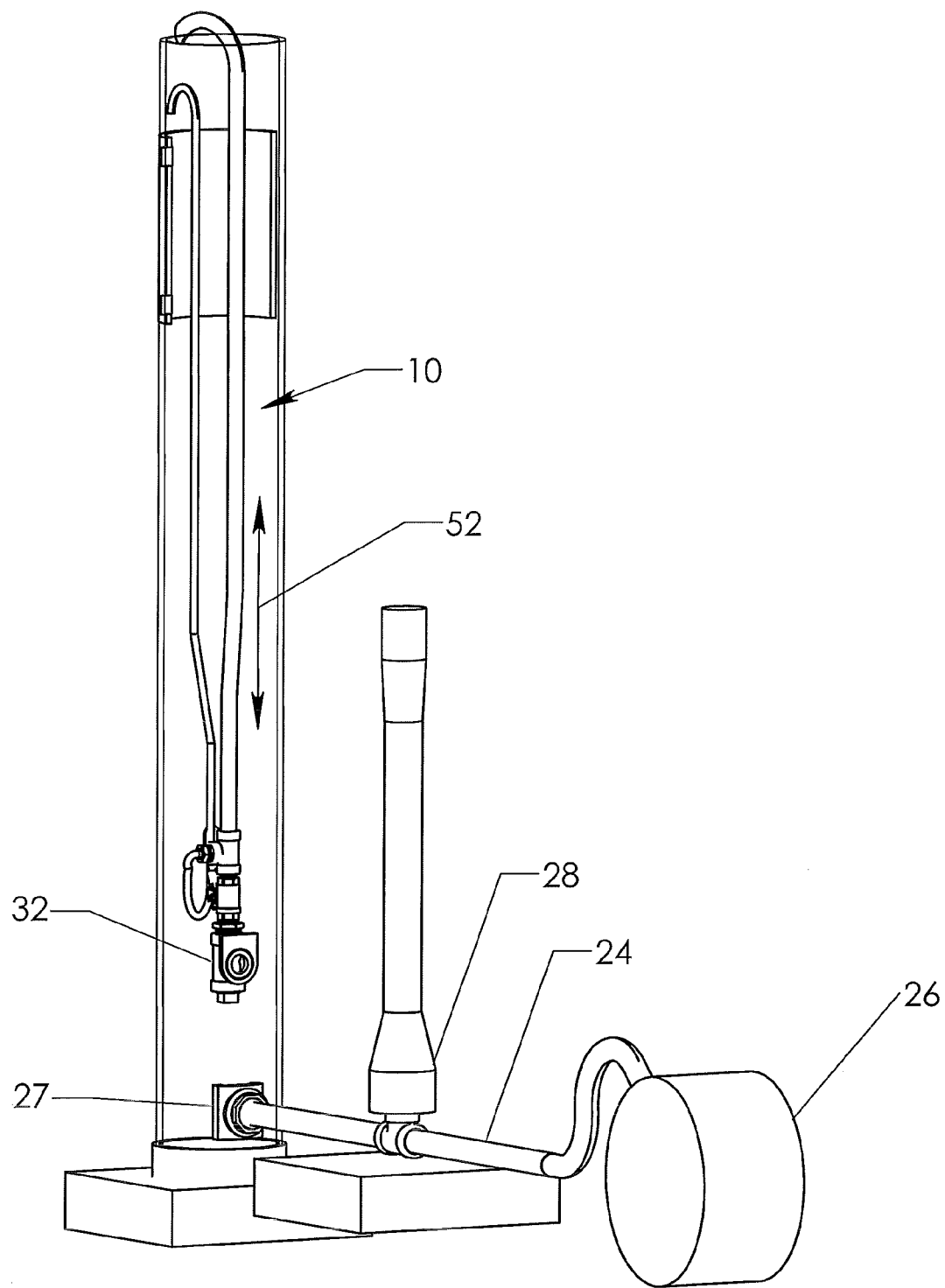
FIG. 2 shows the sampling device of the present invention being moved either to or from an operative position and FIG. 3 shows the sampling device in operative position.
Figure 3:
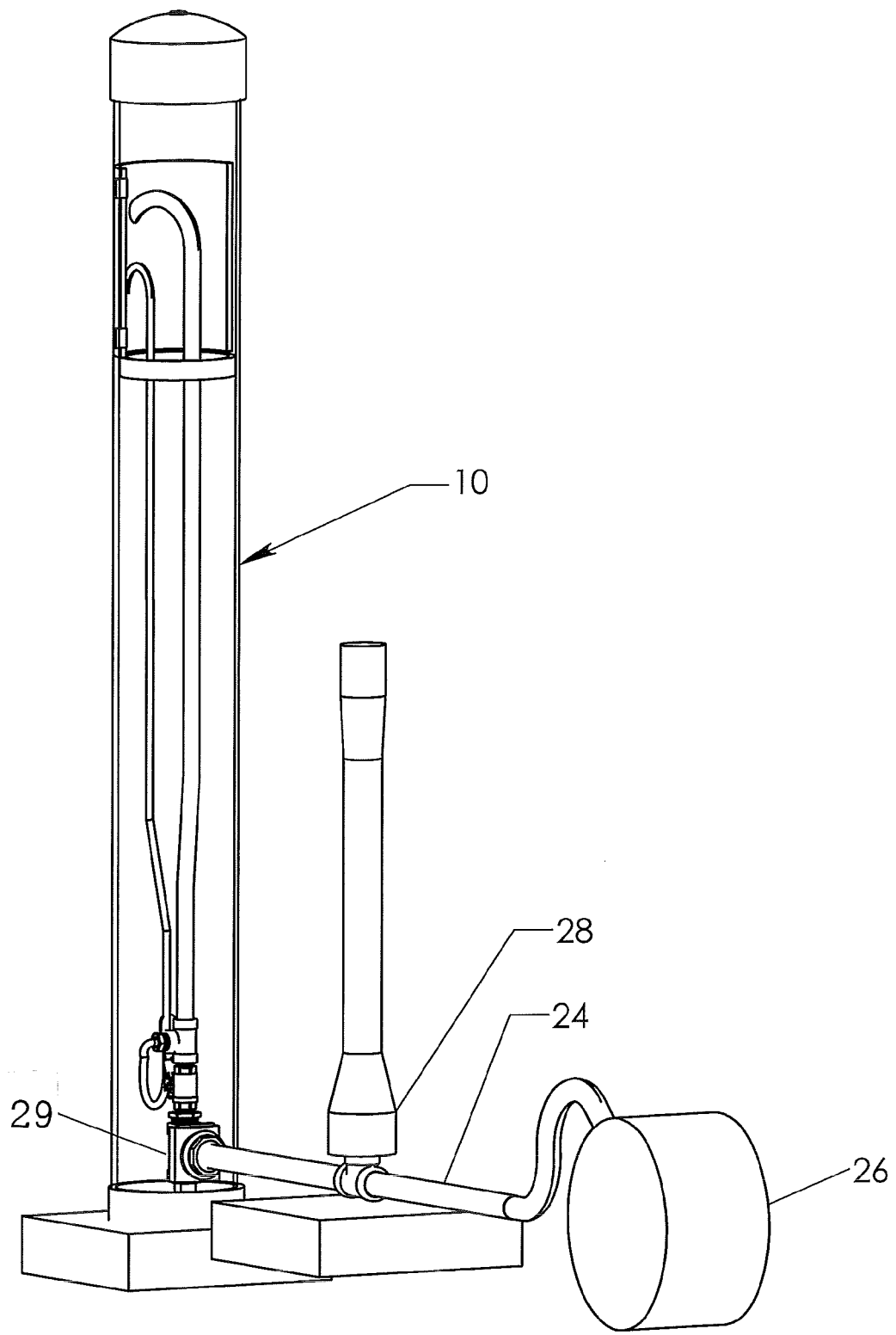

The sample device 10 of the present invention is shown in a sampling station 12 in operative position with the device 10 in operative position. The station 12 is formed by a stationary or fixed casing 14 which in the illustrated arrangement is formed by a circular cross section sleeve 16 having and bottom cap 18 and a removable top cap 20 and an access opening 22 through the sleeve 16. The casing 14 is positioned in a test site so that the bottom 16 is below the incoming branch line 24 (see FIGS. 2 and 3). The branch line 24 carries water (or other fluid) from the main line 26 to the sample station 12 and has an inlet valve 28 interposed between the sample station 12 and the main line 26 to control flow through the branch line 24. One side 27 of a releasable coupling formed by the side 27 and the side 32 described below combine when the device 10 is in operative position to form a coupling 29 between the device 10 and the branch line 24 (see FIG. 3).

Figure 1:
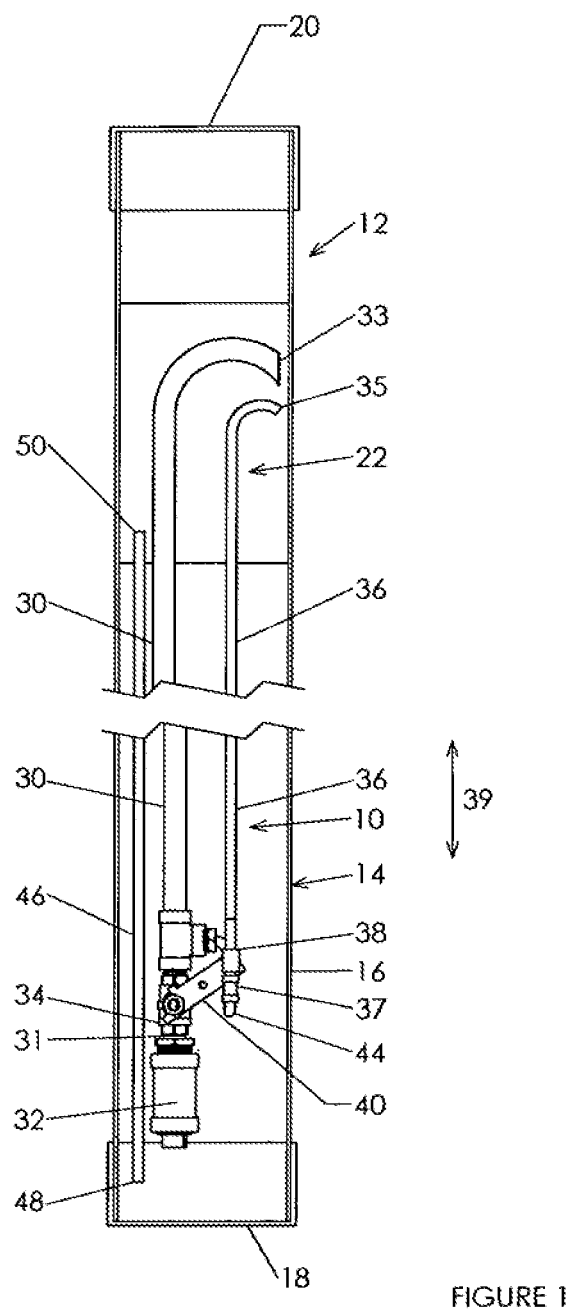
FIG. 1 is a schematic cross section through a test sample station illustrating the sampling device in operative position.

The sample device 10 as shown in more detail in FIG. 1 has a rigid (shape retaining and not easily bent) main tube 30 that is connected at one end 31 to a sampling valve 34 (preferably a ball valve) the opposite side of which is connected to the other side 32 of the releasable coupling 29 (which preferable is a coupling referred to in the trade as a pit-less adapter).

A rigid operating tube 36 is connected as indicated at 38 adjacent to one end 37 of the tube 36 to an operating lever 40 of the valve 34 so that movement of the tube 36 as indicated by the arrow 39 operates the valve 34 and moves it between open and closed positions. The main and operating tubes 30 and 36 have their ends 33 and 35 remote from their one ends 31 and 37 in close proximity and position to be easily accessible through the access opening 22 of the casing 14.

Connected to the end 37 of the tube 36 is a flexible tube 44 which connects to the tube 30 adjacent to its end 31 i.e. adjacent to the valve 34 thereby interconnecting the tubes 30 and 36 to permit flow of fluid (water) there-between.

A suitable drain tube 46 preferably forms part of the device 10 i.e. is connected in any suitable manner to the device 10 so that it is moved into position with the device 10. This drain tube 46 has one end (lower or bottom end) 48 that when in operative position extends to the bottom of the casing 14 and an opposite end 50 which is in close proximity to the opposite ends 33 and 35 of the tubes 30 and 36.

In operation the device 10, if not already in position, is positioned in the casing 14 by removing the top cap 20 and inserting the device 10 as indicated by the arrow 52 and coupling the two halves 25 and 32 to complete the coupling 29 and interconnect the branch line 24 with the device 10. The valve 28 is then opened to permit flow to the device 10 from the main line 26. When a sample is to be taken the stiff tube 36 is manipulated to open the sampling valve 34 and the water flows through the main tube 30 so that a sample may be collected. The sample valve 34 is then closed and the stiff tube 36 may be connected to suitable pump to pump water from the main tube 30. Water may be pumped through the drain line 46 to empty the casing 14 either before or after the sampling operation is performed.

The device 10 may be removed as indicated by the arrow 52 and serviced and/or taken to another sampling site.

Having described the invention, modifications will be evident to those skilled in the art without departing from the scope of the invention as defined in the appended claims.

I claim:

1. A sampling system comprising a sample obtaining device for use in a sampling station, said device comprising a main tube, a first portion of a releasable coupling connected to one end of said main tube via a sampling valve, an operating lever for said valve, a operating tube connected adjacent to one end of said operating tube to said operating lever so that movement of said operating tube moves said sampling valve between an open and a closed position, a main tube emptying line connecting said one end of said operating tube to said main tube at a location immediately adjacent to said sampling valve and opposite ends of said main and operating tubes are spaced from their respective one ends and to permit access thereto when said device is in operative position.

2. A sampling system comprising a sample obtaining device for use in a sampling station as defined in claim 1 wherein said sampling system includes a water sampling station that includes a fixed casing wherein said sample obtaining device in operative position is received and each of said opposite ends are accessible through an opening into said casing and a branch inlet line for water to be sampled passes into said casing and mounts a second portion of said releasable coupling to which said first portion is releasably coupled when said device is in operative position.

3. A sampling system comprising a sample obtaining device for use in a sampling station defined in claim 2 wherein said sample obtaining device further includes a drain line that extends from adjacent to said opposite ends to a remote end that is on the side of said first portion of said releasable coupling remote from said main tube.

4. A sampling system comprising a sample obtaining device for use in a sampling station defined in claim 1 wherein said sample obtaining device further includes a drain line that extends from adjacent to said opposite ends to a remote end that is on the side of said first portion of said releasable coupling remote from said main tube.

* * * * *